United States Patent
Okano et al.

(10) Patent No.: US 7,753,054 B2
(45) Date of Patent: Jul. 13, 2010

(54) METHOD OF CONSTRUCTING SPINAL INJURY MODEL MONKEY AND UTILIZATION THEREOF

(75) Inventors: Hideyuki Okano, Tokyo (JP); Yoshiaki Toyama, Tokyo (JP); Masaya Nakamura, Tokyo (JP); Tatsuji Nomura, Tokyo (JP); Yoshikuni Tanioka, Kanagawa (JP); Kiyoshi Ando, Tokyo (JP); Yonehiro Kanemura, Osaka (JP)

(73) Assignees: Japan Science and Technology Agency, Kawaguchi-shi (JP); Keio University, Tokyo (JP)

( * ) Notice: Subject to any disclaimer, the term of this patent is extended or adjusted under 35 U.S.C. 154(b) by 262 days.

(21) Appl. No.: 10/496,993

(22) PCT Filed: Nov. 26, 2002

(86) PCT No.: PCT/JP02/12308

§ 371 (c)(1),
(2), (4) Date: May 27, 2004

(87) PCT Pub. No.: WO03/045137

PCT Pub. Date: Jun. 5, 2003

(65) Prior Publication Data

US 2005/0186545 A1    Aug. 25, 2005

(30) Foreign Application Priority Data

Nov. 29, 2001    (JP)    ............................ 2001-364563

(51) Int. Cl.
*A61B 19/00*    (2006.01)

(52) U.S. Cl. ...................................................... 128/898
(58) Field of Classification Search .................. 128/898
See application file for complete search history.

(56) References Cited

FOREIGN PATENT DOCUMENTS

| JP | 2001-511456 | 8/2001 |
|---|---|---|
| WO | 99/06060 | 2/1999 |

OTHER PUBLICATIONS

Hotz "Adult Tissue Can Yield Stem Cells, Researchers Say", www.mult-sclerosis.org/news/Nov2000/StemCellsFromAdults.html, Nov. 6, 2000.*

(Continued)

*Primary Examiner*—Thomas J Sweet
(74) *Attorney, Agent, or Firm*—Oblon, Spivak, McClelland, Maier & Neustadt, L.L.P.

(57) ABSTRACT

A method for creating a monkey model of spinal cord injury, which includes exposing the dura mater of the cervical cord of a monkey and applying a load on the dura mater; the thus-created monkey model of spinal cord injury; and a method for evaluating a therapeutic drug for spinal cord injury by use of this model.

According to the present invention, it is possible to create a monkey which is close to the human and thus useful as a model of human spinal cord injury. This model enables proper evaluation of therapeutic effects of various drugs on spinal cord injury. Through use of this model, it has been confirmed for the first time that transplantation therapy of human neural stem cells is efficacious against spinal cord injury.

4 Claims, 7 Drawing Sheets

OTHER PUBLICATIONS

Lacroix et al "Neurotrophic factors and gene therapy in spinal cord injury" Neurorehabil Neural Repair, 2000;14(4): 265-75.*
Arunkumar et al. "Motor and somatosensory evoked potentials in a primate model of experimental spinal cord injury." Neurol India. Sep. 2001;49(3):219-24.*
Soblosky et al, Graded unilateral cervical spinal cord injury in the rat: evaluation of forelimb recovery and histological effects, Jan. 26, 2001, Behavioural Brain Research, vol. 119, issue 1, pp. 1-13).*
Ehime Medical Journal, vol. 19, No. 2, (2000), pp. 259 to 268.
J. Neurosurg., vol. 59, (1983), pp. 269 to 275.
J. Biomechanics, vol. 25, No. 10, (1992), pp. 1165 to 1172.
Experimental Medicine, vol. 20, No. 9, (2002), pp. 1301 to 1306.
Society for Neuroscience Abstracts, vol. 27, No. 1, (2001), p. 962 & 31st Annual Meeting of the Society for Neuroscience San Diego, USA Nov. 10-15, 2001.
Spine, vol. 20, No. 21, (1995), pp. 2318 to 2327.
Pamela S. Diener, et al., The Journal of Neuroscience, vol. 18, No. 2, pp. 779-793 Jan. 15, 1998.
Pamela S. Diener, et al., The Journal of Neuroscience, vol. 18, No. 2, pp. 763-778 Jan. 15, 1998.
V.R. Edgerton, et al., Abstract Viewer/Itinerary Planner Washington, DC: society for Neuroscience, 2003. CD-ROM. Program No. 71.5.
M.J.Garcia-Miguel, et al., Abstract Viewer/Itinerary Planner Washington, DC: society for Neuroscience, 2003. CD-ROM. Program No. 275.4.
E. Schmidlin, et al., Abstract Viewer/Itinerary Planner Washington, DC: society for Neuroscience, 2003. CD-ROM. Program No. 275.9.
H.Yang, et al., Abstract Viewer/Itinerary Planner Washington, DC: society for Neuroscience, 2003. CD-ROM. Program No. 954.16.
E. Emery, et al., Journal of Neuroscience Research, vol. 62, pp. 821-829 2000.
Song Liu, et al., J. Neurosurg, (Spine 1), vol. 94, pp. 82-90 2001.
Yuuto Ogawa, et al., "Transplantation of Neural Stem Cells for Treating Traumatic Spinal Cord Injury" J. Jpn. Orthop. Assoc., 74 (8), 2000, pp. 1-4 (with English Translation).

* cited by examiner

METHOD OF CONSTRUCTING SPINAL INJURY MODEL MONKEY AND UTILIZATION THEREOF

TECHNICAL FIELD

The present invention relates to a method for creating a monkey model of spinal cord injury, a monkey model obtained by use of the method, and a method for evaluating a therapeutic drug for spinal cord injury by the use of the monkey model.

BACKGROUND ART

The cause of a spinal cord injury may be either traumatic or non-traumatic. Spinal cord injuries of the former type are caused by, for example, traffic accidents, sporting accidents, or workplace accidents, whereas those of the latter group are caused by, for example, inflammation, bleeding, tumors, or deformed vertebrae. Most spinal cord injuries are traumatic. Symptoms of spinal injuries include motor function disorders and sensory disturbances.

Spinal injuries are treated primarily by symptomatic therapy by use of a neuroprotective agent or a brain metabolism enhancer, and no therapy can restore neurons lost by spinal cord injury.

Meanwhile, we have seen progress in neuroscience related to spinal cord injury. Specifically, studies have clarified that in adult spinal injuries, despite the presence of endogenous neural stem cells in the spinal cord, neogenesis of neurons or oligodendrocytes does not occur, permitting differentiation and proliferation of astrocytes and resulting in formation of glial scar, which prevents axonal regeneration.

A single case of successful neural regeneration within damaged spinal cord heretofore reported is a rat spinal cord injury case, where transplantation of a fetal rat spinal cord was performed and found effective (Diener P S and Bregman B S, J. Neurosci., 18(2): 779-793(1998), Diener P S and Bregman B S, J. Neurosci., 18(2), 763-778(1998)).

When application to humans of this single case of success is pursued, large amounts of human fetal spinal cords required for transplantation procedure must be secured. However, procurement of such massive human fetal spinal cords is not realistic and is actually not applicable in practice.

Accordingly, an object of the present invention is to create a spinal cord injury model in an animal which is closer to the human, to thereby provide a method for treating spinal injuries which can be applied to humans.

DISCLOSURE OF THE INVENTION

The present inventors have performed extensive research in an attempt to create a spinal cord injury model using a monkey, and have found that when a monkey is subjected to a surgical operation so as to expose the dura mater of the cervical cord and a load is applied onto the exposed dura mater, the monkey exhibits disturbed motor function similar to that found in human spinal cord injury, and thus is useful as a human spinal cord injury model, and that use of the monkey ensures correct evaluation of spinal cord injury remedies. Furthermore, they have found that transplantation of human neural stem cells in the lesion site of the monkey afflicted with spinal cord injury results in improvement in motor functions and regeneration of neurons. The present invention has been accomplished on the basis of these findings.

Accordingly, the present invention provides a method for creating a monkey model of spinal cord injury characterized by exposing the dura mater of the cervical cord of a monkey and applying a load onto the exposed dura mater, as well as a monkey model of spinal cord injury thus created.

The present invention also provides a method for evaluating a therapeutic drug for a spinal cord injury, characterized by administering a therapeutic drug to a monkey model of spinal cord injury.

Moreover, the present invention provides a method for treating spinal cord injury, characterized in that neural stem cells are transplanted into a lesion site of the spinal cord.

BEST MODE FOR CARRYING OUT THE INVENTION

No particular limitations are imposed on the monkeys which are employed as the spinal cord injury model of the present invention, and examples include prosimians such as lemurs, indri, aye aye, loris, and tarsius; and anthropoids such as marmosets, cebus, cercopithecus, hylobates, and *P. pygmaeus*. Anthropoids are particularly preferred.

In order to create a monkey model of spinal cord injury, firstly, the dura mater of the cervical cord of a monkey is exposed. This operation is performed under anesthesia. Briefly, the hair of the back side of the monkey's neck is shaven, and any of the vertebral arches of the cervical vertebrae (C1-C7) is extracted, to thereby expose the dura mater. Preferably, the extraction is performed on any one of the C3 to C7 cervical vertebrae.

Figure 1:
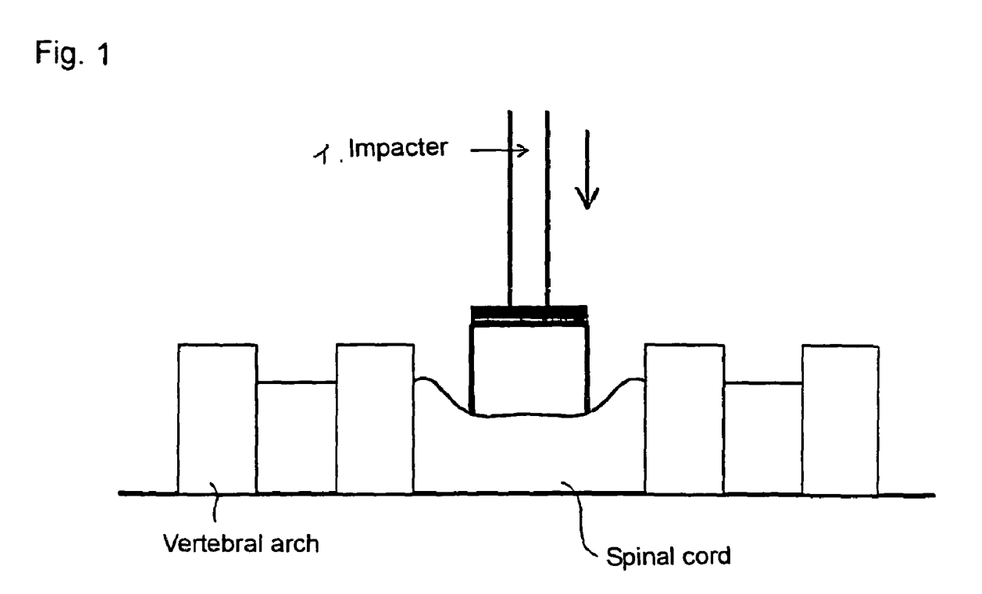
FIG. 1 is a conceptual chart showing the state where a load is applied onto the spinal cord.

A load is applied to the exposed dura mater, to thereby give damage to the spinal cord (see FIG. 1). In consideration of creating a model mimicking human spinal cord injury, preferably, a load of 15 to 25 g is allowed to fall from 20 to 60 mm above, more preferably a load of 18 to 25 g is allowed to fall from 30 to 60 mm above. To ensure application of a certain load from a certain height by way of falling, use of an impacter is preferred.

The surgical site of the monkey that has received damage to its spinal cord under a load is sutured.

The thus-obtained monkey model of spinal cord injury shows clear injury in the spinal cord by MRI imaging or tissue staining, and the injury is not healed over a long period of time.

Also, the monkey model of spinal cord injury shows motor function disorders resembling those developed by human patients suffering spinal cord injury. The presence of motor function disorders is definitely substantiated from an overall evaluation regarding ability to move around, ability to perform revolving motions, retention of seated posture, behavior to take a standing posture, ability to jump, ability to reach for an object, ability to reach for feed, gripping ability, etc. More specifically, in response to a stimulus of "feeding," among other disorders, behavior to reach for the feed and ability to grasp something are clearly deteriorated.

As described above, the monkey model of spinal cord injury according to the present invention develops symptoms similar to those of human spinal cord injury, making the model useful for the evaluation of a therapeutic drug for human spinal cord injury. For example, evaluation as to whether or not a certain test drug has a therapeutic effect may be performed by administering the drug to this monkey model and monitoring pathological conditions over time.

Examples of the test drug include factors having neuroregenerative activity (including low molecular compounds), a variety of neurotrophic factors, neural growth factors, and neural growth promoting substances. Examples of administration routes include not only oral administration and injection, but also direct administration to the injury site, and transplantation.

Examples of means for monitoring pathological conditions over time include monitoring improvement in the aforementioned motor functions, MRI, and electromyogram.

The present inventors have found that transplantation of human neural stem cells to the injury site of the monkey model induces regeneration of neurons in the injury site, clearly improving the conditions of disordered motor functions and other disorders.

The human neural stem cells which may be employed include, but are not limited to, those developed through the neurosphere method by Weiss, et al. (Science 255: 1707-1710 (1992)). The timing at which the neural stem cells are to be transplanted is any time after creation of the spinal cord injury. In consideration of the viability and differentiation of the transplanted neural stem cells, transplantation is effective if performed at one or two weeks after spinal cord injury. This point is critical in clinical application.

The count of cells to be transplanted is preferably $10^5$ to $10^6$. Transplantation may be performed once or several times. Also, a variety of neurotrophic factors, such as BDNF (brain-derived neurotrophic factor), NT-3 (Neurotrophin-3), etc. may be co-employed in an amount of 20 ng.

As a more specific transplantation method, neural stem cells may be injected into the cavity of the injury site. Alternatively, stem cells may be subjected to three-dimensional culture in collagen gel so as to induce cell differentiation in advance, followed by transplantation together with the gel into the injury site.

EXAMPLES

The present invention will next be described in more detail by way of examples, which should not be construed as limiting the present invention thereto.

Example 1

Creation of a Monkey Model of Spinal Cord Injury (1) Surgical Procedure Performed on a Common Marmoset Under mixed anesthesia using a combination of xylazine hydrochloride and ketamine hydrochloride or inhalation anesthesia using isoflurane, the 5th and 6th cervical vertebrae are excised to thereby expose the dura mater. A 20-g weight is allowed to fall from a height of 50 mm onto the dura mater at the level of the 5th cervical vertebra, thereby creating a cervical cord injury model. An artificial dura mater is overlaid on the dura mater at the site of laminectomy, followed by surgical wound closure. After the damage was imparted, the animal's bladder was manually drained until the bladder function is improved, and antibiotics are administered as needed in order to prevent infection.

(2) MRI Images and Tissue Staining Images before and after Spinal Cord Injury

Figure 2:
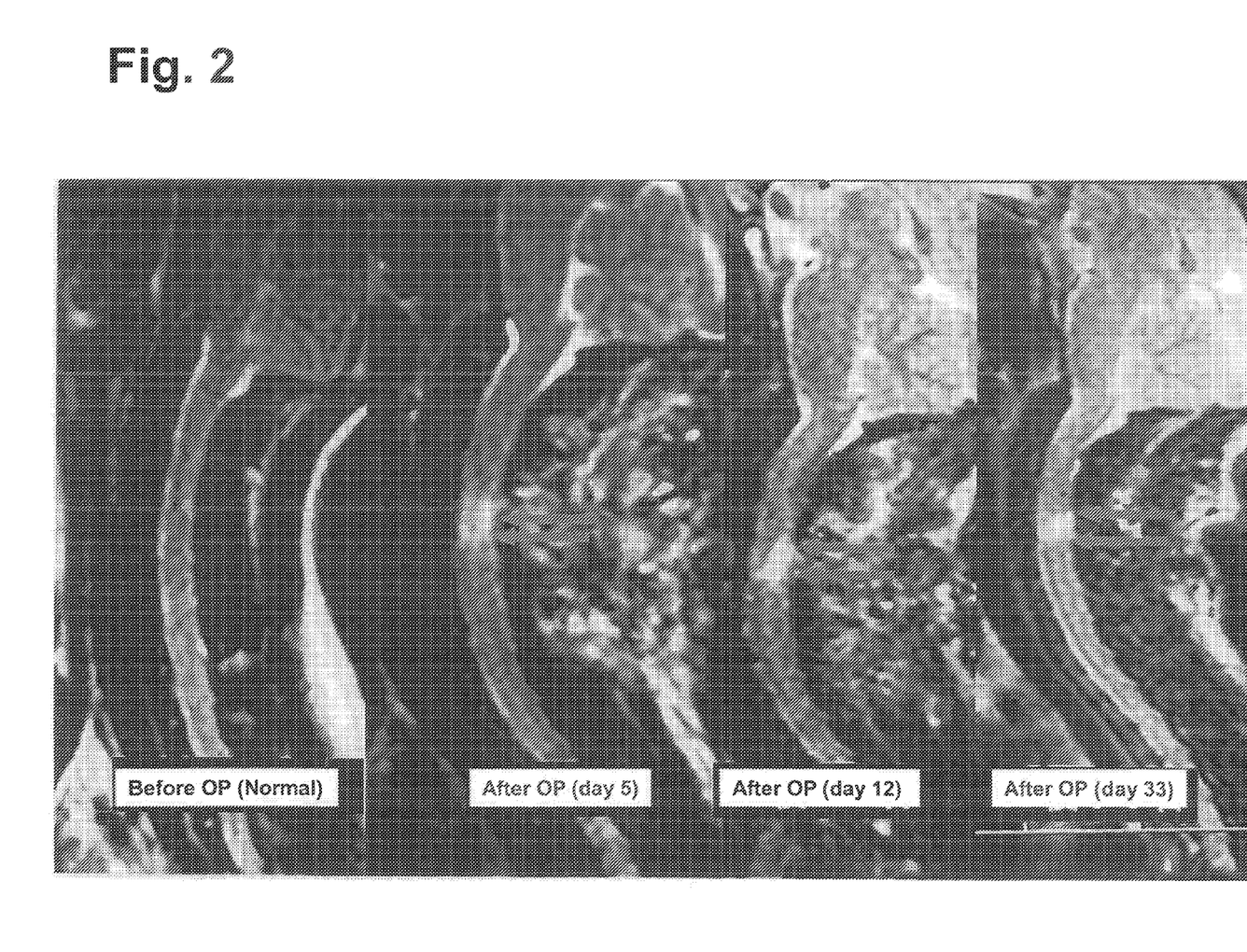
FIG. 2 shows MRI images captured before and after the incident of spinal cord injury.
Figure 3:
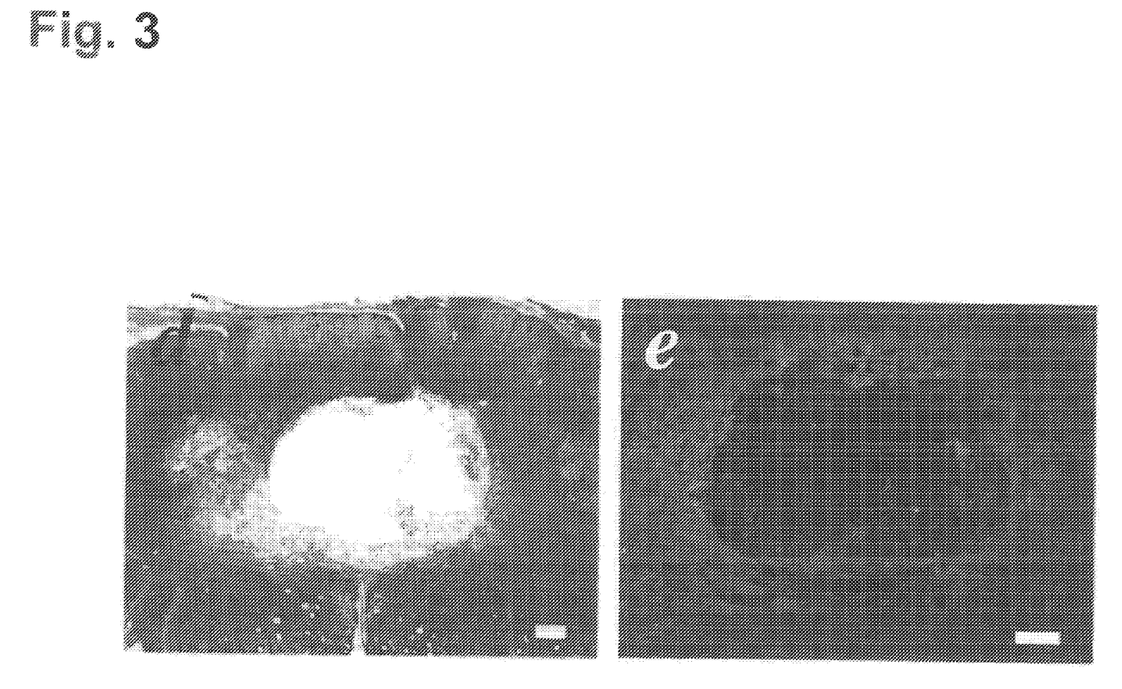
FIG. 3 shows a routine tissue staining (hematoxylin-eosin) image of a cross section of the spinal cord after spinal cord injury (left); and a double staining image using GFAP (green)/β-tublin III (red) (right)

FIG. 2 shows MRI images captured before and after creation of spinal cord injury in a marmoset (20 g, 50 mm). The images show that the injury that was not present before operation exists even 33 days after the operation, presenting definite evidence of spinal cord injury. FIG. 3 shows a routine tissue staining (hematoxylin-eosin) image of a cross section of the spinal cord after spinal cord injury (left); and a double staining image using GFAP (glial fibrillary acidic protein) (green)/β-tublin III (red) (right). The images show a cavity in the spinal cord and show that neurons are lost.

Figure 5:
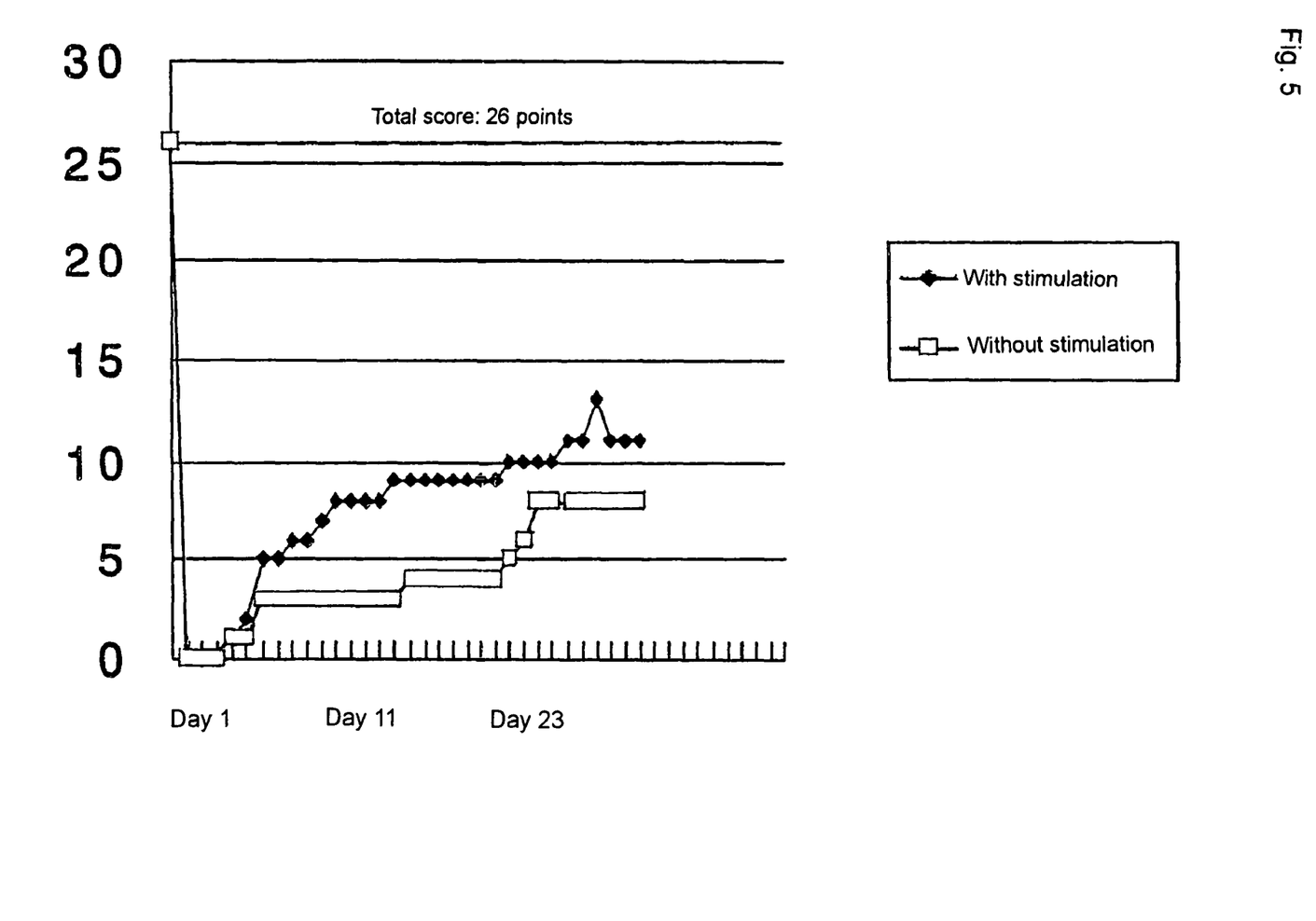
FIG. 5 shows the progress courses of disordered motor functions of marmosets with spinal cord injury.

(3) In accordance with the evaluation items shown in Table 1, motor functions were evaluated, with the maximum score being 26 points. Before evaluation a stimulus was given to the animal by way of, for example, feeding or extending a bar in front of the animal's face, and judgment was made as to whether the animal responds to the stimulus with sound motor functions. The results are shown in FIG. 5. As is apparent from FIG. 5, the injured marmoset under conditions of 20 g-50 mm exhibited a protracted disorder in motor functions over a prolonged period of time.

TABLE 1

Evaluation Table for Motor Functions of a Marmoset Model of Spinal Cord Injury

Moves around using:

the right forelimb
the left forelimb
the right hind limb
the left hind limb
Moves around in the cage without falling through grids
Makes turning movements on a flat plane
Retains seated posture
Stands with its buttocks raised
Jumps
Makes a continuous jumping movement
Extends its forelimbs when lying
Tries to reach for an object in front of him by raising:

the right forelimb
the left forelimb
Grasps the feed by using:

the right forelimb
the left forelimb
Climbs the cage using:

the right forelimb
the left forelimb
the right hind limb
the left hind limb
Holds the perch
Clings to the bars of the cage by using:

the right forelimb
the left forelimb
the right hind limb
the left hind limb
Changes its posture from lying on its back to lying on its stomach.
Jumps from bar to bar accurately in the cage.
Total (out of 26 points)

Example 2

Human Neural Stem Cell Transplantation Therapy (1) Neural stem cells were transplanted to a marmoset which had received a spinal cord injury as described in Example 1. Specifically, a 5 µL solution containing human neural stem cells in an amount of $1 \times 10^5/\mu l$ was injected, over 10 minutes, into the cavity of spinal injury site of the marmoset which was in the tenth day of injury-imparting operation and had been confirmed to have motor function disorders (transplantation group). As a control, injection of a culture medium alone (5 µl) was employed (non-transplantation group).

(2) Motor functions were monitored for 7 days after transplantation. No clear difference was observed in terms of improvement in motor functions between the transplantation group and the non-transplantation group. When 10 weeks had passed after transplantation, significant improvement in forelimb motor functions was observed in the transplantation group as compared with the non-transplantation group; that is, with respect to the forelimb muscles and reaching motion (reaching for food), remarkable recovery was observed (FIG. 5) in the transplantation group.

Figure 4:
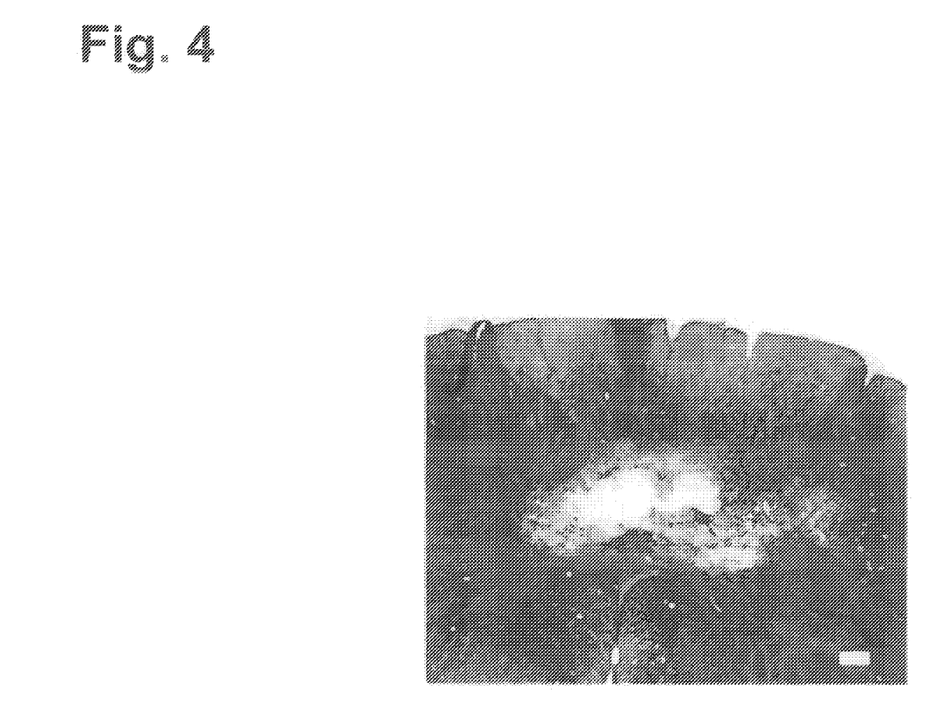
FIG. 4 shows a routine tissue staining image (hematoxylin-eosin staining) of a cross section of spinal cord 8 weeks after neural stem cell transplantation.

(3) FIG. 4 shows a routine tissue staining image (hematoxylin-eosin staining) of a cross section of the spinal cord 8 weeks after transplantation. As compared with the left side image in FIG. 3, more neural tissues attained through neural stem cell transplantation can be seen.

Figure 6:
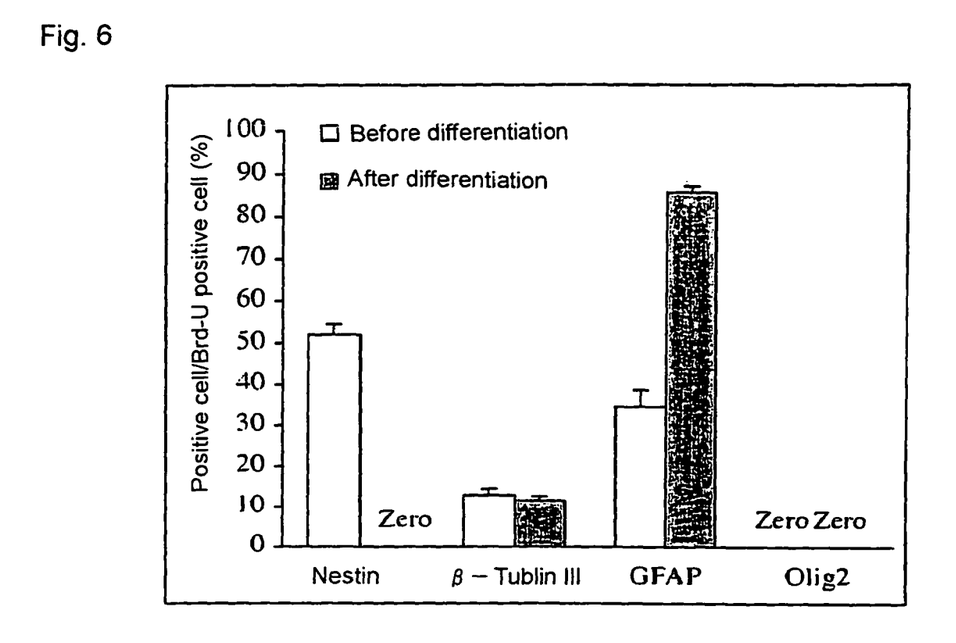
FIG. 6 is a chart showing the in vitro differentiation of human neural stem cells into different types of cells.
Figure 7:
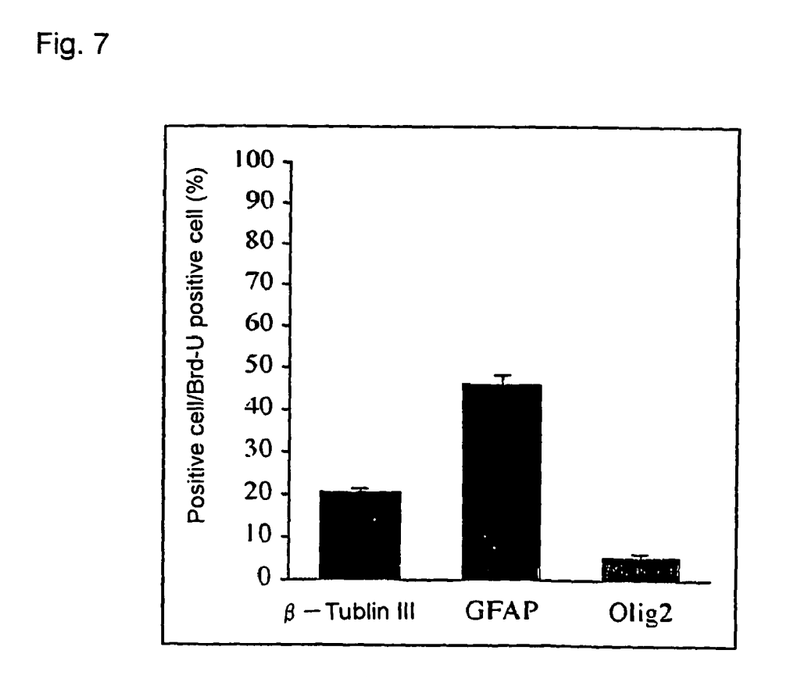
FIG. 7 is a chart showing the differentiation of human neural stem cells which have been transplanted into a spinal cord injury lesion.

(4) FIG. 7 shows the results of differentiation of human neural stem cells as determined after 8 weeks of transplantation. The cells had been differentiated into β-tublin III, GFAP (glial fibrillary acidic protein), and Olig 2 (oligodentrocytes). The results greatly differ when compared to the differentiation state where human neural stem cells were induced to differentiate in vitro (FIG. 6).

(5) The transplanted cells were found to have been successfully engrafted in the injury site, with many cells identified in craniocaudal directions. From FIGS. 4 and 6, the transplanted cells were determined to have been differentiated into neurons, oligodendrocytes, and astrocytes.

Figure 8:
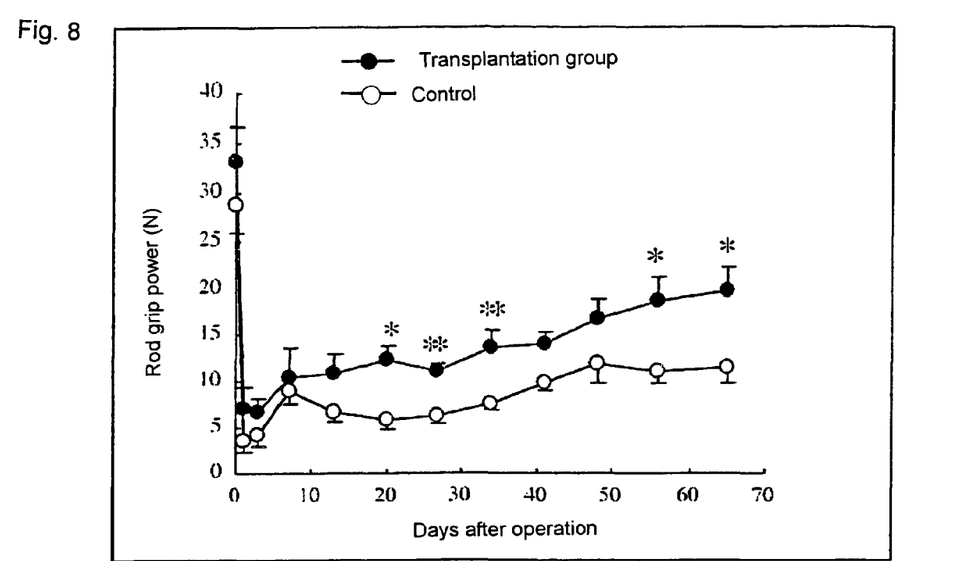
FIG. 8 is a chart showing the recovery in ability of gripping a bar after transplantation of human neural stem cells.

(6) Recovery of ability to grip a bar after human neural stem cell transplantation was measured (bar grip test: J. Neurosci. Methods 62, 15-19 (1995)). As compared with the non-transplantation group, the transplantation group was found to have significantly recovered bar grip ability (FIG. 8).

Figure 9:
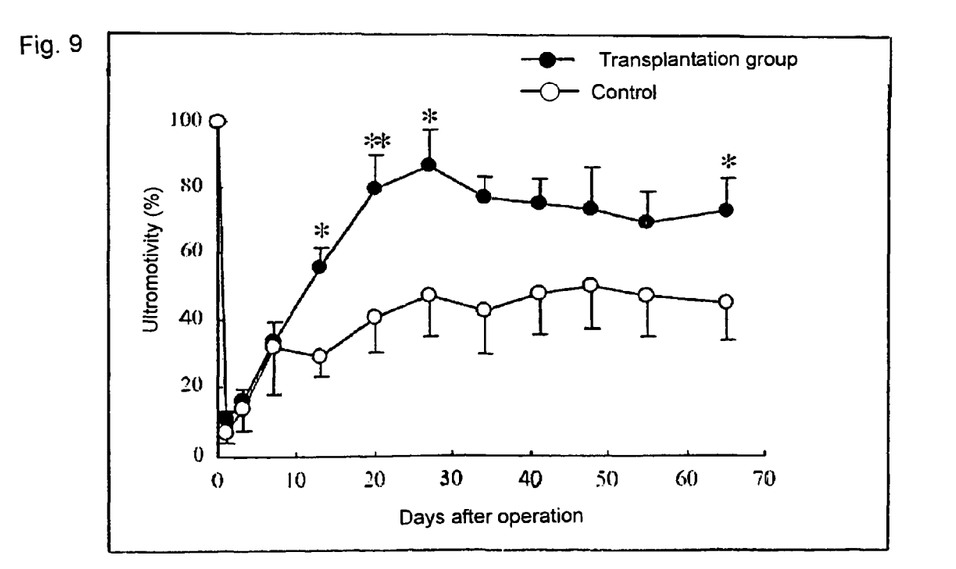
FIG. 9 is a chart showing the recovery in spontaneous motor activity following human neural stem cell transplantation.

(7) Recovery of ultromotivity after human neural stem cell transplantation was measured by use of an infrared sensor system. As compared with the non-transplantation group, the transplantation group was found to have significantly recovered spontaneous motor activity (FIG. 9).

INDUSTRIAL APPLICABILITY

The present invention has enabled provision of a monkey which is close to the human and is useful as a model of human spinal cord injury. Through use of the model, therapeutic effects of a variety of drugs against spinal cord injury can be properly evaluated. Use of this model has first substantiated that the human neural stem cell transplantation therapy is effective in the treatment of spinal cord injury.

The invention claimed is:

1. A method for creating a monkey model of cervical spinal cord injury, comprising exposing the dura mater of the cervical cord of a monkey and applying a load onto the exposed dura mater of the cervical cord region, wherein the load weighs 15 to 25 g and is applied by being caused to fall from 20 to 60 mm above the dura mater, wherein the monkey model exhibits a protracted disorder in motor function compared to a monkey to which the load has not been applied.

2. The method according to claim 1, wherein the monkey in which spinal cord injury has been created has a motor function disorder which is comparable to that of human spinal cord injury.

3. The method according to claim 1, wherein said dura mater is exposed by excising any one of the C3 to C7 cervical vertebrae.

4. The method according to claim 1, wherein the protracted disorder of motor function is at least one member selected from the group consisting of limb movement, turning movement, seated posture, standing, jumping, extension of forelimbs, reaching with forelimb, grasping an object with forelimb, climbing, holding with limb, and combinations thereof.

* * * * *